United States Patent
Baxi et al.

(10) Patent No.: US 9,568,432 B2
(45) Date of Patent: Feb. 14, 2017

(54) SENSOR APPARATUS TO DETERMINE A VALUE OF A CHEMICAL PARAMETER BASED ON A COLOR SHADE AND METHODS THEREOF

(71) Applicant: Intel Corporation, Santa Clara, CA (US)

(72) Inventors: Amit S. Baxi, Thane (IN); Vincent S. Mageshkumar, Navi Mumbai (IN)

(73) Assignee: Intel Corporation, Santa Clara, CA (US)

( * ) Notice: Subject to any disclaimer, the term of this patent is extended or adjusted under 35 U.S.C. 154(b) by 132 days.

(21) Appl. No.: 14/497,384

(22) Filed: Sep. 26, 2014

(65) Prior Publication Data

US 2016/0091433 A1   Mar. 31, 2016

(51) Int. Cl.
| | | |
|---|---|---|
| *G01N 21/78* | (2006.01) | |
| *G01N 21/25* | (2006.01) | |
| *G01N 21/80* | (2006.01) | |
| G01N 21/01 | (2006.01) | |
| G01N 21/77 | (2006.01) | |

(52) U.S. Cl.
CPC ............ *G01N 21/78* (2013.01); *G01N 21/251* (2013.01); *G01N 21/255* (2013.01); *G01N 21/80* (2013.01); *G01N 2021/0181* (2013.01); *G01N 2021/7773* (2013.01); *G01N 2201/0627* (2013.01); *G01N 2201/0635* (2013.01); *G01N 2201/125* (2013.01); *G01N 2201/13* (2013.01)

(58) Field of Classification Search
CPC ............... G01N 2021/0181; G01N 2021/7773; G01N 21/251; G01N 21/255; G01N 21/78; G01N 21/80; G01N 2201/0627; G01N 2201/0635; G01N 2201/125; G01N 2201/13

USPC ........ 436/164, 169, 103, 108, 128, 133, 163, 436/23, 79, 86, 95, 97; 422/400, 401, 422/420, 82.05, 82.09, 403
See application file for complete search history.

(56) References Cited

U.S. PATENT DOCUMENTS 6,798,517 B2 *  9/2004  Wagner .................... G01J 3/02
                                                356/406
7,577,469 B1 *  8/2009  Aronowitz ......... A61B 5/14532
                                                600/310

(Continued)

FOREIGN PATENT DOCUMENTS

KR   10-2008-0052349 A   6/2008

OTHER PUBLICATIONS

International Search Report and Written Opinion received for PCT Application No. PCT/US2015/047658, mailed Nov. 27, 2015, 12 pages.

*Primary Examiner* — Maureen Wallenhorst
(74) *Attorney, Agent, or Firm* — Jordan IP Law, LLC

(57) ABSTRACT

Apparatus and methods may provide for determining a value of chemical parameter. One or more light emitters may be positioned within a housing to emit light through an aperture of the housing. The emitted light may illuminate a color area of a structure that is separable from the housing, such as a test strip, a printed color reference, and so on. A color sensor may be positioned within the housing to capture reflected light and to convert the reflected light to an initial digitized color space that may be usable to determine a color shade of a color area. The reflected light may, for example, be captured independently at least of a dimension (e.g., predetermined size, shape, etc.) of the color area.

27 Claims, 6 Drawing Sheets

(56) References Cited

U.S. PATENT DOCUMENTS

| | | | |
|---|---|---|---|
| 7,623,240 B2* | 11/2009 | Rudolf | G01N 21/255 356/39 |
| 2004/0152209 A1 | 8/2004 | Zin et al. | |
| 2009/0147262 A1* | 6/2009 | Huang | G01N 21/314 356/445 |
| 2013/0267032 A1 | 10/2013 | Tsai et al. | |
| 2014/0134052 A1 | 5/2014 | Stevenson et al. | |
| 2014/0170757 A1* | 6/2014 | Tsai | G01N 21/78 436/55 |
| 2014/0273052 A1 | 9/2014 | Reddy et al. | |

* cited by examiner

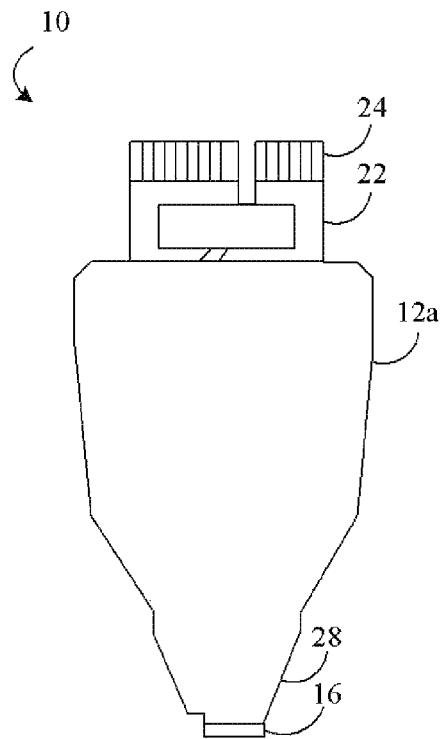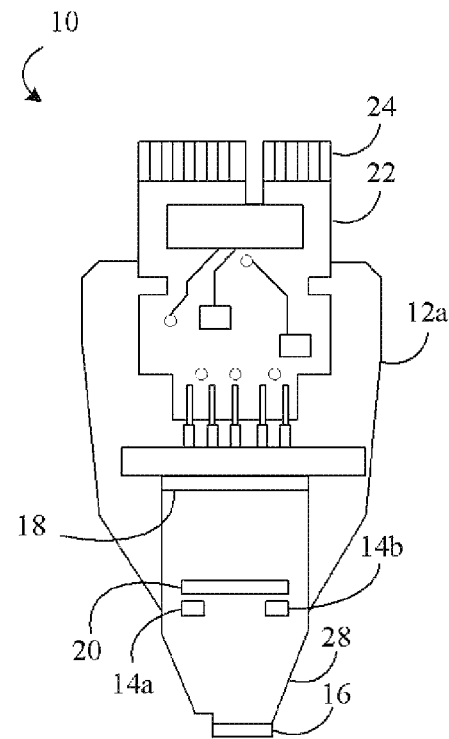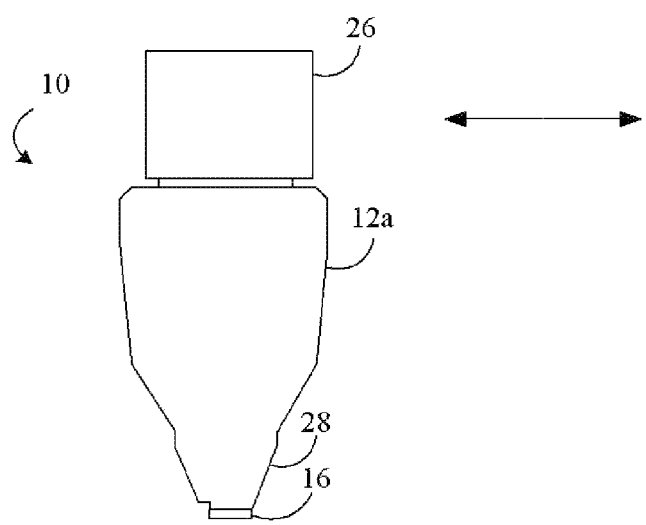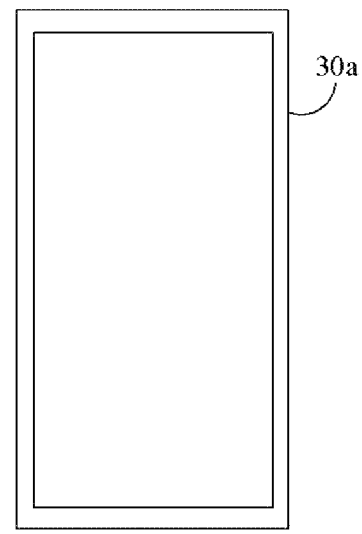
FIG. 1A  FIG. 1B
FIG. 1C

SENSOR APPARATUS TO DETERMINE A VALUE OF A CHEMICAL PARAMETER BASED ON A COLOR SHADE AND METHODS THEREOF

TECHNICAL FIELD

Embodiments generally relate to chemical sensors. More particularly, embodiments involve a sensor apparatus that is to determine a value of a chemical parameter based on a color shade and methods thereof.

BACKGROUND

Chemical compounds may be measured using an ion-sensitive electrode. However, the ion-sensitive electrode may be unattractive for on-the-go or point-of use chemical testing since it may be relatively expensive or fragile (e.g., glass electrodes). The ion-sensitive electrode may also require relatively frequent calibration, activating solutions or reagents, and/or relatively onerous travel or storage conditions.

Chemical compounds may also be measured using chemically coated test strips that change color based on a concentration of a chemical compound detected. Test strips may be unreliable, however, since a user may need to visually compare a developed color shade with a reference chart, which impacts consistency and/or repeatability. Also, only qualitative results (e.g. low, medium, high) may be available due to relatively limited color shades. Color shades of a test strip that fall between two adjacent shades on a reference chart may not be reliably interpreted, or values for intermediate color shades may not be quantified. Brightness or color tinge of ambient light falling on a test-strip and/or a color shade chart may also affect consistency and/or repeatability. Also, a developed color shade may be relatively transient and may need to be read relatively quickly (e.g., about 30 seconds to 40 seconds) before it changes color.

Color reader devices (e.g., a colorimetric glucometer) may utilize a test strip with a color sensitive area on which a drop of blood is deposited to provide a color shade based on glucose concentration. The strip may be inserted into the color reader device to read the developed color and quantify blood glucose. Such reader devices may only be capable of reading a single type of test strip (e.g., a test strip of specified size, shape, and/or dimensions, with relatively limited parameters), and may not be used to read or interpret any other types of off-the-shelf test strips, other types of parameters, and so on.

BRIEF DESCRIPTION OF THE DRAWINGS

The various advantages of the embodiments will become apparent to one skilled in the art by reading the following specification and appended claims, and by referencing the following drawings, in which:

FIGS. 1A-1C are illustrations of an example disaggregated sensor apparatus according to an embodiment;

DESCRIPTION OF EMBODIMENTS

Figure 2:
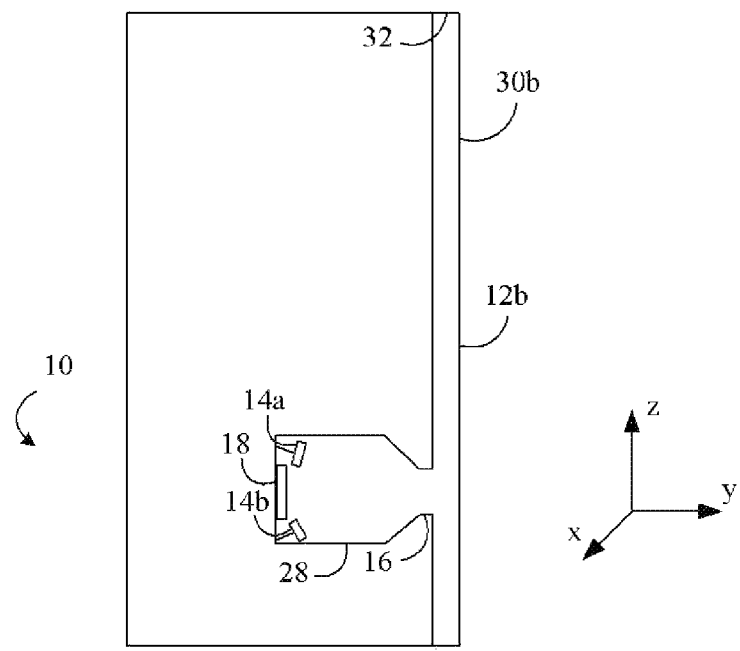
FIG. 2 is an illustration of an example sensor apparatus according to an embodiment.

Turning now to FIGS. 1A-1C, a sensor apparatus 10 is shown that may provide a versatile and scalable solution to automatically and accurately read, interpret, interpolate, and/or quantify results from substantially any type of off-the-shelf chemical test strip. The sensor apparatus 10 includes a housing 12a that may be formed in any geometrical shape or of any material. For example, the housing 12a may include a cone portion, discussed below, and/or may be formed of a metal material, an alloy material, a polymer material, a ceramic material, and so on. A light emitter 14 (14a-14b) is positioned within the housing 12a and faces a structure (not shown) that is separable from the housing 12a. The structure may include a test structure, such as a paper-based test strip, which is chemically coated to form one or more color areas that are intended to change color and form developed shades (e.g., sensed shades) based on a concentration of a chemical compound (e.g., analyte, target, reactant, etc.) when contacted with a fluid having the chemical compound. The structure may also include a reference structure, such as a printed color reference (e.g., color shade chart), including one or more color areas that are not intended to contact a fluid to change color but rather include reference shades intended for comparison with developed shades to determine a value of a chemical parameter (e.g., pH, etc.) based on developed shades.

In one example, the light emitter 14 emits white light through an aperture 16 (e.g., having any shape including a square shape, a round shape, etc.) of the housing 12a to illuminate a color area of the structure. In addition, a color sensor 18 is positioned within the housing 12a and faces the aperture 16 to read a color shade of a color area, such as a color intensity (e.g., a shade of color) of the color shade (e.g., developed shade, reference shade, etc.). For example, a color shade may be read when light from the light emitter 14 is reflected back from the color area through the aperture 16 and arrives at the color sensor 18. As described in detail below, the color sensor 18 converts the reflected light to an initial digitized color space that may subsequently be used to determine a shade of color, a qualitative value of a chemical parameter, a quantitative value of a chemical parameter, and so on. Thus, reading a color shade may include capturing light, converting light to an initial digitized color space, and/or determining a color.

A lens 20 is positioned within the housing 12a between the light emitter 14 and the sensor 18, which may substantially limit the field of view of the color sensor 18 to that of the aperture 16. In addition, the housing 12a includes a logic module 22 (e.g., printed circuit board (PCB)). As discussed in detail below, the logic module 22 may include logic to interpret, interpolate, and/or quantify results. For example, the logic module 22 may include a command module, a timer module, a demarcation module, a reference generation module, a normalization module, a reference retrieval module, a color space transformation module, a match module, and/or a value storage module.

In the illustrated example, the logic module 22 includes a communication interface 24 that couples with a communication module 26 to forward data wirelessly to a computing platform external to the housing 12a. The computing platform may include, for example, a desktop computer, notebook computer, tablet computer, convertible tablet, personal digital assistant (PDA), mobile Internet device (MID), media player, smart phone, smart televisions (TVs), radios, etc., or any combination thereof. In the illustrated example, the computing platform includes a mobile computing platform 30a (e.g., a smart phone) and the wireless technology includes Bluetooth (e.g., Institute of Electrical and Electronics Engineers/IEEE 802.15.1-2005, Wireless Personal Area Networks).

The logic module 22 may forward an initial digitized color space to an application at a computing platform via the communication module 26 to interpret color shades (e.g., black color, white color, other color), interpolate color shades (if necessary), quantify values (e.g., quantitative, qualitative), display results, store results, and so on. The logic module 22 may interpret color shades, interpolate color shades (if necessary), quantify values, and send that sensor data to the application via the communication module 26 for display of results, storage of results, and so on. Thus, the sensor apparatus 10 may be a disaggregated sensor that is not necessarily packaged (e.g., not integrated) into a customized and targeted strip reader special-purpose embedded device and may be implemented independently of a particular reader device from a particular manufacturer.

In the illustrated example, the aperture 16 is positioned at a narrow end of a cone portion 28 of the housing 12a. In addition, the color sensor 18 is positioned at a wide end of the cone portion 28 of the housing 12a. Moreover, the light emitter 14 is positioned in the cone portion 28 of the housing 12a between the color sensor 18 and the aperture 16. Thus, the sensor apparatus 10 substantially shields the color sensor 18 from ambient light (e.g., via a cone geometry, location of components, etc.). For example, light that is captured by the color sensor 18 substantially includes light that is reflected back from the color area through the aperture 16 and substantially excludes ambient light. In addition, reflected light may pass through the lens 20 (e.g., focusing lens) positioned in the cone portion 28 between the color sensor 18 and the light emitter 14 to further aid in shielding the color sensor 18 from ambient light via a focused field of view.

Notably, a color shade may be read independently of a dimension (e.g., size, shape, etc.) of a color area. For example, pressing the aperture 16 against a color area of a structure may cause the color sensor 18 to read the color shade without regard to a size (e.g., perimeter) of the color area, a shape (e.g., geometry) of the color area, and so on. Accordingly, the sensor apparatus 10 may not be limited to any particular type of test strip and may be used to read a color area/shade for substantially all types of test strips. In addition, the sensor apparatus 10 may be used to read a plurality of color shades independently of a number of color areas, a spacing between two or more color areas, a dimension of a structure (e.g., perimeter, geometry, etc.), a manufacturer of a structure, and so on. The color sensor 18 may, for example, sequentially read a plurality of color shades when the aperture 16 is sequentially placed on each of a plurality of color areas via, e.g., a pick-and-place operation with the apparatus 10 along the surface of the structure, via a sliding operation with the apparatus 10 along the surface of the structure, etc. Thus, reflected light from a color area through the aperture 16 that arrives at the color sensor 18 may be captured independently of a predetermined (e.g., required) dimension of a color area, spacing between two or more color areas, number of color areas, dimension of the structure, and/or manufacturer of the structure.

The sensor apparatus 10 may also provide a relatively quick read of a plurality of developed shades, resulting from a chemical reaction on a test strip, before an undesired change in color. In addition, the sensor apparatus 10 may read a developed shade without regard to a dimension of a color area of a test strip, a number of color areas of a test strip, a dimension of a test strip, and/or a manufacturer of a test strip. The sensor apparatus 10 may also relatively quickly read a plurality of reference shades to generate a digitized reference shade chart without regard to a dimension of a color area of a printed color reference, a number of color areas of a printed color reference, a dimension of a printed color reference, and/or a manufacturer of a printed color reference.

FIG. 2 demonstrates that the sensor apparatus 10 may be integral with a computing platform, such as a mobile computing platform 30b (e.g., a smart phone). In the illustrated example, the sensor apparatus 10 includes a housing 12b that is shared with the mobile computing platform 30b. The aperture 16 is positioned at a narrow end of the cone portion 28, the color sensor 18 is positioned at a wide end of the cone portion 28, and the light emitters 14a, 14b are positioned in the cone portion 28 between the color sensor 18 and the aperture 16 at opposite sides of the color sensor 18. In the illustrated example, the color sensor 18 is shielded from ambient light (e.g., via a cone geometry, location of components, etc.).

A slit 32 is positioned adjacent the aperture 16 and is coupled with the cone portion 28 to accommodate a swipe of a structure through the slit 32. The slit 32 may be positioned to accommodate an insertion of a structure in a single direction (e.g., to read a color shade) along any axis that is perpendicular to a field of view of the color sensor 18, to a direction of the light emitted by the light emitters 14a, 14b, and so on. For example, a user may swipe an entire test strip or printed color reference (e.g., a row thereof, a column thereof, etc.) in a single direction along an axis (e.g., z axis) to read a color shade of a color area. The slit 32 may also include a barrier (e.g., a sidewall perpendicular to a vector of insertion) to accommodate a swipe and/or insertion up to a certain distance.

The slit 32 may be integral with the housing 12b or may be mechanically separable from the housing 12b. For example, the slit 32 may be molded into the housing 12b or otherwise fixed (e.g., soldered, glued, bolted, etc.) to the housing 12b, etc. The slit 32 may also be attached with the housing 12b via a fastener such as a magnet, a clip, etc. Similarly, the slit 32 may be integral with or mechanically separable from the housing 12a (FIGS. 1A-1C), discussed above. In addition, the cone portion 28 may be integral with (e.g., molded, fixed, etc.) the housings 12a, 12b or mechanically separable from (e.g., via a fastener) the housings 12a, 12b. Moreover, the cone portion 28 may be mechanically separable from the slit 32, wherein the cone portion 28 may be coupled with the slit 32 and released as desired. Thus, the sensor apparatus 10 (and/or components thereof) may be mechanically separable from any computing platform. In one particular example, the sensor apparatus 10 is mechanically separable from a mobile computing device via a phone jack communication interface, a bus communication interface (e.g., universal serial bus (USB) interface, PCB interface, etc.), and so on.

Swiping a structure through the slit 32 may place a color area in front of the aperture 16 and cause the color sensor 18 to read a color shade without regard to a size (e.g., perimeter) of the color area, a shape (e.g., geometry) of the color area, and so on. In this regard, the color area may not necessarily contact the aperture 16 although the slit 32 may be selected and/or adjusted to facilitate contact. Thus, the sensor apparatus 10 may not be limited to any particular type of test strip and may be used to read a color area for substantially all types of test strips. Moreover, the sensor apparatus 10 may read a plurality of color shades independently of a number of color areas, a spacing between two or more color areas, a dimension of a structure (e.g., perimeter, geometry, etc.), and/or a manufacturer of a structure. In addition, reagents or activating solutions may not be needed, and the sensor apparatus 10 may provide relatively inexpensive on-the-go and point-of-use fluid testing, without the need for specialized training.

Figure 3:
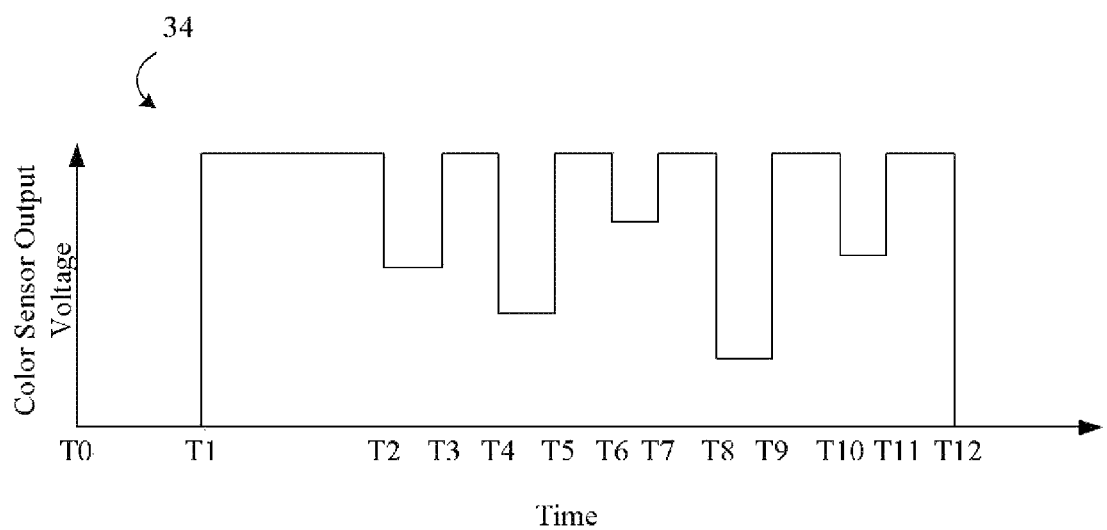
FIG. 3 is a graph of an example output from a color sensor according to an embodiment.

Turning now to FIG. 3, an output 34 from a color sensor is shown according to an embodiment. The color sensor may be housed in a sensor apparatus 10 (FIGS. 1A-1C, FIG. 2, FIG. 3), discussed above. A color sensor may include a color transducer, such as Red-Blue-Green (RGB) color transducer, which may be housed in a cone portion to shield it from ambient light. In addition, a pair of emitters (e.g., white LEDs) mounted inside the cone portion may be used to illuminate a surface of a test strip and/or of a color shade chart to read a color shade for each color area. An aperture at a narrow end of the cone portion may allow light reflected off the surface of the test strip and/or the color chart into the cone portion. The reflected light may pass through a lens, which is used to limit a field of view of the RGB color transducer to that of the aperture. The reflected light may then fall on the RGB color transducer, which converts the reflected light to separate RGB components digitized by an Analog-to-Digital (A/D) converter. Thus, a color sensor may detect a change in intensity (e.g., color) and map the change to a digitized RGB color space. As discussed below, the digitized RGB color space may be subsequently used to determine a quantitative value and/or a qualitative value of a chemical parameter based on a color shade.

In the illustrated example, a color sensor may provide voltage levels that vary with respect to time as a plurality of color shades are encountered and/or read. For example, a white background color of a test strip and/or of a color shade chart may cause a relatively large amount of light to be reflected back into a sensor apparatus and result in a relatively high voltage level from a color sensor. The reflected light may, for example, be used to detect a presence of a structure in a slit, to detect that a sensor apparatus is pressed against a structure, and so on. Alternatively, a black background may cause a relatively small amount of light to be reflected back into a sensor apparatus and result in a relatively low voltage level from a color sensor. The reflected light may, for example, be used to detect an absence of a structure in a slit.

Accordingly, voltage levels between times T0-T1 and at time T12 may be used indicate that a color shade is not being encountered and/or read (e.g., interpreted as a test strip not inserted in a slit, etc.). Similarly, the voltage level between times T1-T2, T3-T4, T5-T6, T7-T8, T9-T10, and T11-T12 may also indicate that a color area is not being encountered and/or read (e.g., interpreted as a white space between color areas). Thus, as a structure passes across a field of view of a color sensor, a change in intensity of light falling on the color sensor may be used to distinguish a gap (or spacing) between different color areas on a test strip and/or a reference color chart to signal when a read is to commence or to end. In addition, voltage levels between times T2-T3, T4-T5, T6-T7, T8-T9, and T10-T11 may be used to indicate that a first color shade, second color shade, third color shade, fourth color shade, and fifth shade, respectively, are being encountered and/or read.

Voltage levels may also be used to determine a qualitative value of a chemical parameter based on a developed shade (e.g., sensed shade). For example, a user may wish to confirm the absence of an analyte in a fluid (e.g., arsenic in drinking water), although trace levels may be tolerable. A change of voltage level in response to a change in color shade for the arsenic parameter (e.g., from a threshold value, from minimum value (e.g., 0), from maximum value (e.g., 1), etc.) may provide a qualitative value to the user (e.g., Arsenic=Δ V=Yes, Present, etc.). In another example, the user may know that a certain level of arsenic in drinking water is tolerable, and a magnitude of voltage level in response to a change in color shade for the arsenic parameter may be mapped to a quantitative value for the arsenic parameter (e.g., Arsenic=0.5 V=10 ppb). Chemical parameter values are not mutually exclusive, and may be rendered together, may be rendered as a hybrid value (e.g., Arsenic=Safe), and so on.

Figure 4:
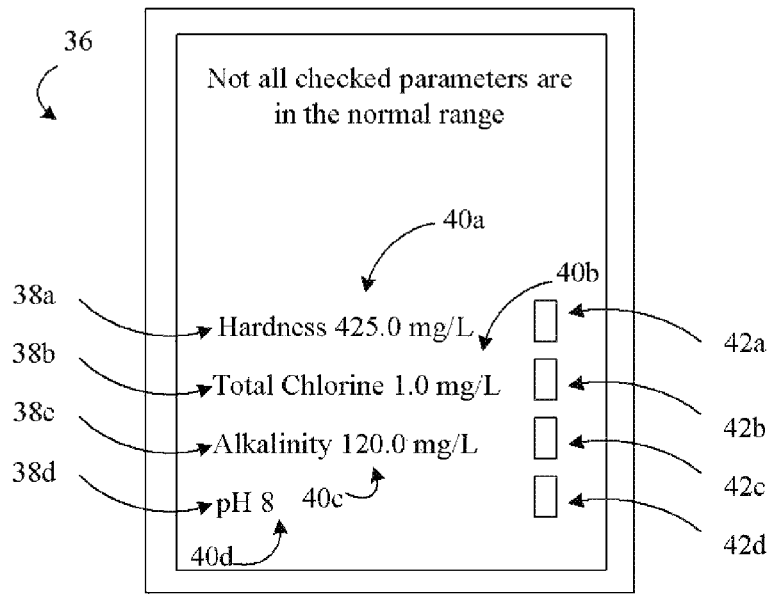
FIG. 4 is an illustration of an example application according to an embodiment.

FIG. 4 shows an application 36 on a computing platform that may display results to a user. The application 36 may provide configurable options to a user. For example, a user may configure which chemical parameters to display, which quantitative values to display, which qualitative values to display, options for each value (e.g., units, relative indicator, etc.), and so on. In the illustrated example, the application 36 displays a set of parameters 38 (38a-38c) together with a corresponding set of quantitative values 40 (40a-40d) and a corresponding set of qualitative values 42 (42a-42d).

For example, the application 36 displays a chemical parameter 38a (water hardness) together with a corresponding quantitative value 40a of 425.0 mg/L for a concentration of an analyte (e.g., a mineral) and a corresponding qualitative value 42a of "red" at an indicator showing that the chemical parameter has a value that is outside of a safe range. The application 36 also displays, for example, a chemical parameter 38d (pH) together with a corresponding quantitative value 40d of 8 for a concentration of an analyte (e.g., hydrogen ions, hydroxide ions) and a corresponding qualitative value 42d of "green" at an indicator showing that the chemical parameter has a value that is within a safe range. The results displayed by the application 36 may be generated using the sensor apparatus 10 (FIGS. 1A-1C, FIG. 2, FIG. 3), discussed above, using voltage levels, discussed above, and/or using a digital representation of test strip and a printed color shade chart, discussed in detail below.

Figure 5:
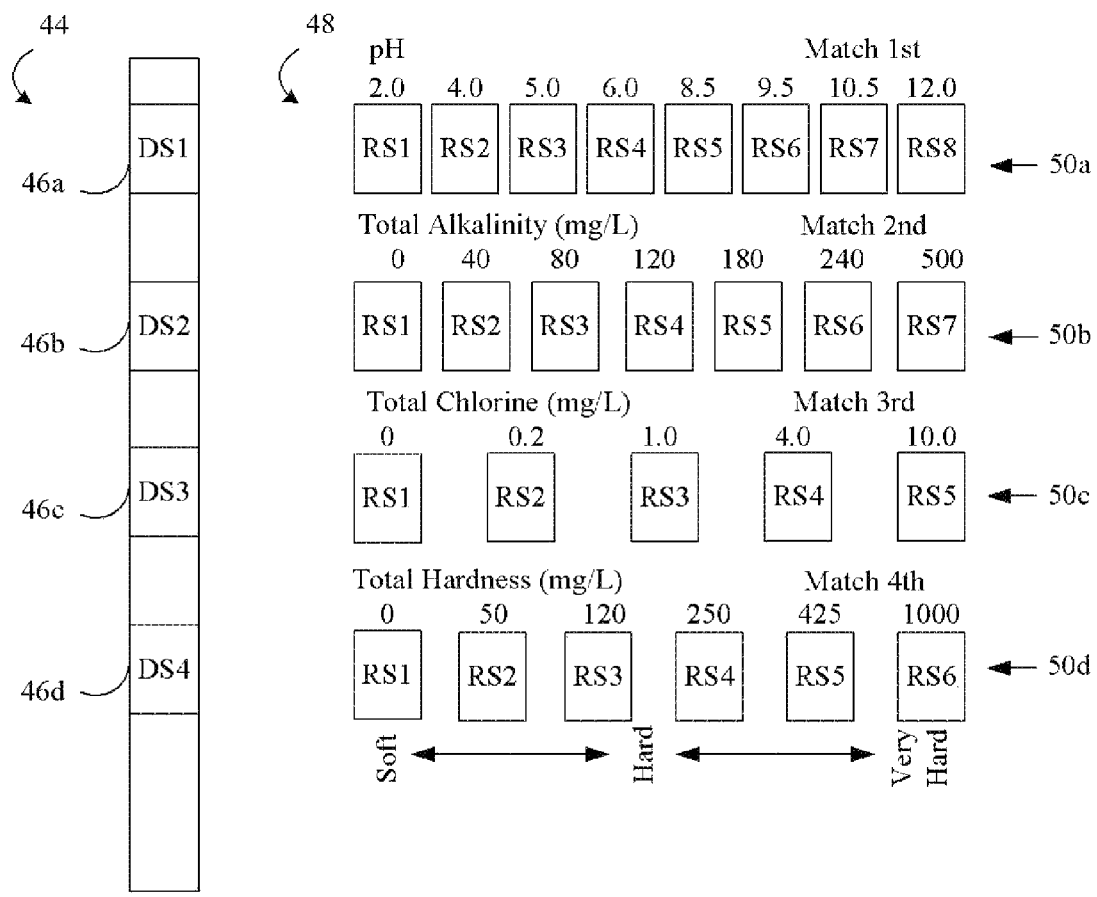
FIG. 5 is an illustration of an example test structure and reference structure according to an embodiment.

Turning now to FIG. 5, a test structure, such as an off-the-shelf test strip 44, is shown that is chemically coated at color areas 46 (46a-46d). Each of the color areas 46 are intended to change color and form developed shades (e.g., sensed shades) based on a concentration of a chemical compound (e.g., analyte, target, reactant, etc.) when contacted with a fluid having the chemical compound. In the illustrated example, the test strip 44 has been submerged in water and retracted, wherein the color area 46a has changed color and formed a developed shade DS1 based on a concentration of hydrogen or hydroxide for a chemical parameter (pH). In addition, the color area 46b has changed color and formed a developed shade DS2 based on a concentration of carbonate and/or bicarbonate for a chemical parameter (alkalinity). Moreover, the color area 46c has changed color and formed a developed shade DS3 based on a concentration of chlorine for a chemical parameter (total chlorine). Additionally, the color area 46d has changed color and formed a developed shade DS4 based on a concentration of a mineral (e.g., calcium, magnesium) for a chemical parameter (water hardness).

The developed color shades may be read by the sensor apparatus 10 (FIGS. 1A-1C, FIG. 2, FIG. 3), discussed above, although substantially any chemical parameter for substantially any fluid may be evaluated using substantially any test strip. For example, an evaluation may be accomplished for ingestible fluids (e.g., milk, oils, pharmaceuticals, etc.), industrial fluids (e.g., wastewater, chemical processing fluids used in, e.g., semiconductor fabrication, auto part manufacturing, etc.), gasoline, etc., cleaning fluids (e.g., detergents), biological fluids (e.g., urine samples, blood samples, saliva sample, etc.), and so on. Thus, measuring chemical compounds in water (e.g., nitrate, chlorine, pH, carbonates, etc.) may help to determine whether water is safe, measuring chemical compounds in urine (e.g., urea, nitrogen, proteins, glucose, ketones, bilirubin) may help to determine a health state for prevention and/or treatment, measuring chemical components in soil filtrate (e.g., nitrogen, phosphorus, potassium) or other conditions (e.g., pH, alkalinity, nitrates) may drive fertilizer distribution levels or other agricultural considerations for optimal crop or animal stock yield. In addition, water quality testing may be provided (e.g. using crowd sourcing for creating water quality maps of different parts of the world, assign quality ratings to water suppliers/restaurants, etc.).

A reference structure, such as a printed color reference 48 (e.g., color shade chart), includes color areas 50 (50a-50d) that are not intended to contact a fluid to change color but rather include reference shades intended for comparison with developed shades of color areas 46a-46d to determine a value of a chemical parameter based on each developed shade. For example, the color area 50a includes a plurality of reference shades RS1-RS8 for a chemical parameter (pH), which are mapped to quantitative values (numerical pH values). In addition, the color area 50b includes a plurality of reference shades RS1-RS7 for a chemical parameter (alkalinity), which are mapped to quantitative values (numerical alkalinity values). Moreover, the color area 50c includes a plurality of reference shades RS1-RS5 for a chemical parameter (total chorine), which are mapped quantitative values (numerical chlorine values). Additionally, the color area 50d includes a plurality of reference shades RS1-RS6 for a chemical parameter (water hardness), which are mapped to quantitative values (numerical hardness values) and to quantitative values (e.g., relative values of soft, hard, very hard). The test strip 44 may be read and compared to a digital representation of the printed color reference 48 to determine qualitative values and/or qualitative values of chemical parameters based on color shades for the color areas 46. For example, DS1 may be read by a color sensor to generate digitized color space values for DS1, which are compared to digitized color space values for RS1-RS8 of 50a to determine a quantitative pH value 2.0, 4.0, etc., for a fluid. Notably, a pH value, e.g., between 2.0 and 4.0 may also be determined, discussed below.

Figure 6:
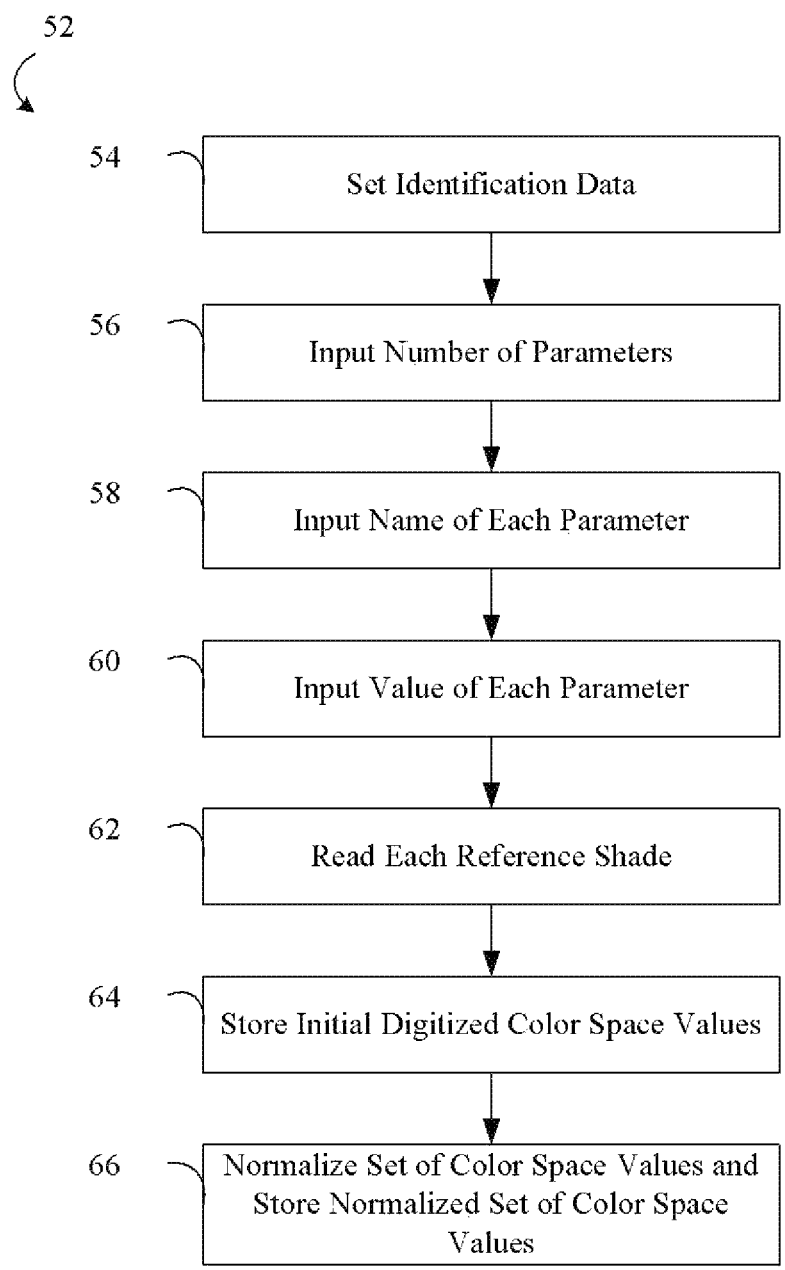
FIG. 6 is a flowchart of an example of a method to create a digital representation of a printed color reference according to an embodiment.

FIG. 6 shows a method 52 of creating a digital representation of a printed color reference according to an embodiment. The method 52 may be implemented using a sensor apparatus such as, for example, the sensor apparatus 10 (FIGS. 1A-1C, FIG. 2, FIG. 3), already discussed. The method 52 may be implemented as one or more modules in a set of logic instructions stored in a machine- or computer-readable storage medium such as random access memory (RAM), read only memory (ROM), programmable ROM (PROM), firmware, flash memory, etc., in configurable logic such as, for example, programmable logic arrays (PLAs), field programmable gate arrays (FPGAs), complex programmable logic devices (CPLDs), in fixed-functionality hardware logic using circuit technology such as, for example, application specific integrated circuit (ASIC), complementary metal oxide semiconductor (CMOS) or transistor-transistor logic (TTL) technology, or any combination thereof.

Illustrated processing block 54 provides for setting identification data associated with, e.g., the printed color reference 48 (FIG. 5), discussed above. For example, a smart phone application may be launched to input identification data including a name, a label, and/or a category for a new digitized reference shade chart. In addition, the processing block 54 provides for setting identification data associated with, e.g., the test strip 44 (FIG. 5), discussed above. For example, a smart phone application may be launched to input identification data including test strip details, such as a test strip manufacturer, a test strip catalog number, a test strip serial number, a test strip name, and so on. The identification data may be input automatically, may be entered by a user in response to a prompt, via a menu, etc.

Processing block 56 provides for inputting a number of chemical parameter that a test strip measures. For example, the number is four (N=4) for the test strip 44 (FIG. 5), discussed above. Processing block 58 provides for inputting a name of each chemical parameter (e.g., pH, alkalinity, chlorine, hardness), and a number of reference shades (e.g., M=8 for pH) for each chemical parameter (e.g., for i=1 to N). Processing block 60 provides for inputting a quantitative value of each chemical parameter (e.g., 2.0, 4.0, 5.0, 6.5, 8.5, 9.5, 10.5, 12.0 for pH) for each reference shade (e.g., for j=1 to M). The processing block 60 may also provide for inputting qualitative values of each chemical parameter for each reference shade (e.g., acidic, neutral, basic).

Processing block 62 provides for reading each reference shade (e.g., $j^{th}$ shade) of each color area for each parameter (e.g., $i^{th}$ parameter) to determine an initial digitized color space (e.g., RGB values/components). In this regard, a plurality of color shades may be read sequentially, such as when a sensor apparatus is picked-and-placed sequentially on each of a plurality of color areas of a structure (e.g., a printed color reference), when a sensor apparatus is swiped (e.g., slid) across a surface of a structure including a plurality of color areas, when a structure including a plurality of color areas is swiped (e.g., slid, inserted, etc.) through a slit coupled with a color sensor, and so on. The read may be accomplished independently of a dimension of a color area, a spacing between two or more color areas, a number of color areas, a dimension of a structure, and/or a manufacturer of the structure. In addition, the read may be relatively fast.

For example, a sensor apparatus may be a wireless accessory device that operates in conjunction with the application 36 (FIG. 4), discussed above, residing on a computing platform (e.g., smartphone, tablet, etc.). A user may successively position the sensor apparatus on each color area (e.g., of a printed color reference) and click a button on the sensor apparatus. For example, the user may position the color sensor in a pre-defined sequence on each color area on the strip (e.g., to allow an application to know what parameter is being sensed) and measure the developed shades by clicking a button on the color sensor or an application. With each click, a color sensor reads a color shade (e.g., reference shade). Thus, a user command that modulates a switch may be detected to read the color shade of the color area.

In another example, a color transducer (e.g., color sensor), an emitter (e.g., LEDs), and a housing (e.g., a cone portion) may be integral with a computing platform (e.g., smart phone) having a slit on a side thereof to accommodate the printed color reference. As a printed color reference is swiped in front of a color sensor (e.g., in front of an aperture of a housing) through the slit, the color sensor detects a presence of the printed color reference by a change in intensity and/or color of reflected light. In addition, the swipe may be in a predetermined direction (e.g., to allow an application to know what parameter is being sensed). Moreover, an expiration of a timer may be detected to read the color shade of the color area (e.g., an expiration of a timer that is set based on an amount of time to pick-and-place a sensor, swipe a color shade chart through a slit, amount of time that it takes for one color area to be replaced by an adjacent color area, etc.). In addition, a demarcation interval may be detected to read the color shade of the color area (e.g., determining the presence of white space between color areas to halt reading, to prepare to read, etc.).

Processing block 64 provides for storing the initial digitized color space values (e.g., RGB values/coordinates). For example, RGB values may be stored locally on memory of a sensor apparatus, remotely on a mobile computing platform, and so on. The method may iteratively loop back as needed to, e.g., the processing block 50, the processing block 60, etc. Stored RGB values may be retrieved for further processing. In addition, a color sensor may deliver RGB values for further processing without storing the RGB values. Processing block 66 provides for normalizing a set of values of the initial digitized color space and storing the normalized set of values. In one example, the set of RGB values may be normalized and stored as a two-dimensional matrix. For example, the set of values of the initial digitized color space (e.g., RGB values) may be stored in a two-dimensional matrix that includes a color space value set (e.g., RGB) in a first dimension and a chemical parameter-reference shade set (e.g., (i)(j)) in a second dimension to store a qualitative and/or quantitative (e.g., [R(i)(j), G(i)(j), B(i)(j)]).

Accordingly, the two-dimensional matrix may be generated by a manufacturer of a test strip, by a user of a test strip at a point-of-use in real time, and so on. In addition, the two-dimensional matrix may be stored and used as a digitized reference shade chart by subsequent users of the same test strip. The digitized reference shade chart may, for example, reside in a cloud computing environment or may be downloaded to a computing device from a test strip manufacturer's website, e.g., when a user purchases a test strip. For example, a quick response (QR) code may be scanned and/or a hypertext protocol link (e.g., HTTP link) may be selected to download the digitized reference shade chart. Moreover, RGB values may be converted to a different color space in real-time and/or values of a final digitized color space may be stored as a digitized reference shade chart that is accessible by subsequent users of the same test strip.

Figure 7:
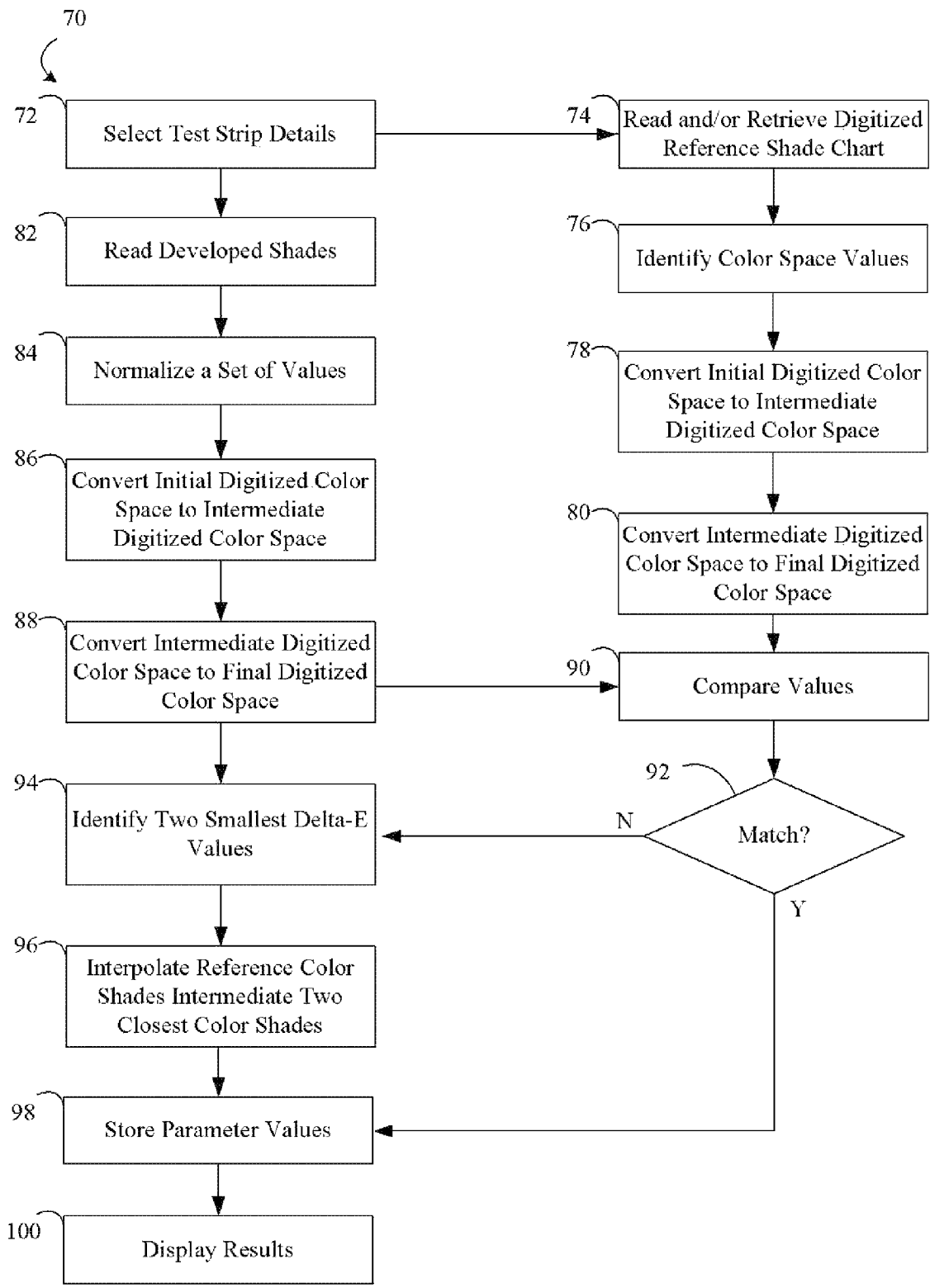
FIG. 7 is a flowchart of an example of a method to sense a color developed by a test structure and match the developed color with a digitized reference shade chart according to an embodiment.

Turning now to FIG. 7, a method 70 of sensing a color developed by a test structure (e.g., test strip) and matching the developed color with a digitized reference shade chart is shown according to an embodiment. The method 70 may be implemented using a sensor apparatus such as, for example, the sensor apparatus 10 (FIGS. 1A-1C, FIG. 2, FIG. 3), already discussed. The method 70 may be implemented as one or more modules in a set of logic instructions stored in a machine- or computer-readable storage medium such as RAM, ROM, PROM, firmware, flash memory, etc., in configurable logic such as, for example, PLAs, FPGAs, CPLDs, in fixed-functionality hardware logic using circuit technology such as, for example, ASIC, CMOS or TTL technology, or any combination thereof.

Illustrated processing block 72 provides for selecting test strip details, such as a test strip name. The test strip details may be input automatically, or may be entered by a user in response to a prompt, via a menu, etc. For example, the test strip may be selected from a cascading drop-down menu that identifies the name of the test strip from a category for the test strip (e.g., ingestible fluid) using the application 36 (FIG. 4), discussed above. The test strip may also be identified automatically using, for example, a QR code or a predetermined setting (e.g., based on time of day, location of a user, etc.). Processing block 74 provides for reading and/or retrieving a test strip's reference shade chart. For example, one or more processing blocks of the method 52 (FIG. 6), discussed above, may be implemented in response to the test strip identification.

Processing block 76 provides for identifying color space values, such as initial digital color space values and/or final color space values, which may be stored. In one example, a user may make a selection of all, or a subset of, developed shades and the initial digital color space values (e.g., RGB values/coordinates) that are identified may be limited based on the selection. In another example, all stored color space values for a digitized color chart may be automatically identified independently of whether a user is interested in all of the chemical parameters sensed by a test strip. Processing block 78 provides for converting an initial digitized color space (e.g., a RGB color space including a set of RGB values) for a digitized reference shade chart to an intermediate digitized color space (e.g., an international commission of illumination (CIE XYZ) color space including a set of XYZ values), discussed below. Processing block 80 provides converting an intermediate digitized color space (e.g., a CIE color space including a set of CIE XYZ values) for the digitized reference shade chart to a final digitized color space (e.g., a Lab color space including a set of L,a,b values), discussed below.

Processing block 82 provides for reading developed shades. For example, each a developed shade of each color area for each parameter may be read to determine an initial digitized color space (e.g., sensing RGB values/components). In this regard, a plurality of color shades may be read sequentially, such as when a sensor apparatus is picked-and-placed sequentially on each of a plurality of color areas of a structure (e.g., a test strip), when a sensor apparatus is swiped (e.g., slid) across a surface of a structure including a plurality of color areas, when a structure including a plurality of color areas is swiped (e.g., slid, inserted, etc.) through a slit coupled with a color sensor, and so on. The read may be accomplished independently of a dimension of a color area, a spacing between two or more color areas, a number of color areas, a dimension of a structure, and/or a manufacturer of the structure. In addition, the read may be relatively fast, such as before a developed shade changes color.

For example, a sensor apparatus may be a wireless accessory device that operates in conjunction with the application 36 (FIG. 4), discussed above, residing on a computing platform (e.g., smartphone, tablet, etc.). A user may dip a test strip in a solution that is under test, retract the test strip, and allow the color areas to generate developed shades based on the solution under test (e.g., wait a predetermined amount of time based on a manufacturer's protocol for the solution under test.). For example, chemically coated areas on the test strip (each corresponding to a chemical parameter) may develop a color shade proportional to the concentration/magnitude of a chemical parameter to which it is sensitive. A user may successively position the sensor apparatus on each color area (e.g., of a test strip) and click a button on the sensor apparatus. For example, the user may position the color sensor in a pre-defined sequence on each color area on the strip (e.g., to allow an application to know what parameter is being sensed) and measure the developed shades by clicking a button on the color sensor or an application. With each click, a color sensor reads a color shade (e.g., developed shade). Thus, a user command that modulates a switch may be detected to read the color shade of the color area.

In another example, a color transducer (e.g., color sensor), an emitter (e.g., LEDs), and a housing (e.g., a cone portion) may be integral with a computing platform (e.g., smart phone) having a slit on a side thereof to accommodate the test strip. As the test strip is swiped in front of a color sensor through the slit, the color sensor detects a presence of the test strip by a change in intensity and/or color of reflected light. In addition, the swipe may be in a predetermined direction (e.g., to allow an application to know what parameter is being sensed). Moreover, an expiration of a timer may be detected to read the color shade of the color area (e.g., an expiration of a timer that is set based on an amount of time to pick-and-place a sensor, swipe a test strip through a slit, amount of time that it takes for one color area to be replaced by an adjacent color area, etc.). In addition, a demarcation interval may be detected to read the color shade of the color area (e.g., determining the presence of white space between color areas to halt reading, to prepare to read, and so on).

Processing block 84 provides for normalizing a set of values of an initial digitized color space. A set of initial digitized color space values (e.g., from developed shades of test strip color areas) may be normalized as follows:

Sensor delivers Rx, Gx, Bx (e.g. RGB values from sensor). Normalize the received values to 0 to 255 (Mr, Cr, Mg, Cg, Mb and Cb are slopes and Y-intercepts of a linear equation (y=mx+c) respectively). We normalize these values against a black and a white calibration reference while calibrating the color sensor. We consider black as 0,0,0 and white as 255, 255, 255 when a black color sheet and white color sheet, respectively, is held in front of the sensor.

$Ry=Mr*Rx+Cr$ $Gy=Mg*Gx+Cg$ $By=Mb*Bx+Cb$

Processing block 86 provides for converting an initial digitized color space (e.g., a RGB color space including a set of RGB values) for, e.g., the test strip to an intermediate digitized color space (e.g., a CIE XYZ color space including a set of XYZ values). An initial digitized color space may be converted to an intermediate digitized color space as follows:

Convert RGB values to CIE XYZ values. Converting to CIE XYZ space may be an intermediate step in converting RGB color space to LAB color space.

```
var_R = ( Ry / 255 )
var_G = ( Gy / 255 )
var_B = ( By / 255 )
if ( var_R > 0.04045 ) var_R = ( ( var_R + 0.055 ) / 1.055 ) ^ 2.4
else                   var_R = var_R / 12.92
if ( var_G > 0.04045 ) var_G = ( ( var_G + 0.055 ) / 1.055 ) ^ 2.4
else                   var_G = var_G / 12.92
if ( var_B > 0.04045 ) var_B = ( ( var_B + 0.055 ) / 1.055 ) ^ 2.4
else                   var_B = var_B / 12.92
var_R = var_R * 100
var_G = var_G * 100
var_B = var_B * 100
X = var_R * 0.4124 + var_G * 0.3576 + var_B * 0.1805
Y = var_R * 0.2126 + var_G * 0.7152 + var_B * 0.0722
Z = var_R * 0.0193 + var_G * 0.1192 + var_B * 0.9505
```

Processing block 88 provides for converting an intermediate digitized color space (e.g., a CIE XYZ color space including a set of CIE XYZ values), e.g., for the test strip to a final digitized color space (e.g., a Lab color space including a set of L,a,b values). Such a conversion may more closely emulate visual perception of a user, and/or may provide more reliable results relative to a visual comparison.

Convert the XYZ color space to Lab Space (International Commission on Illumination/CIE 1994).

```
var_X = X / ref_X   //ref_X = 95.047
var_Y = Y / ref_Y   //ref_Y = 100.000
var_Z = Z / ref_Z   //ref_Z = 108.883
if ( var_X > 0.008856 ) var_X = var_X ^ ( 1/3 )
else                    var_X = ( 7.787 * var_X ) + ( 16 / 116 )
if ( var_Y > 0.008856 ) var_Y = var_Y ^ ( 1/3 )
else                    var_Y = ( 7.787 * var_Y ) + ( 16 / 116 )
if ( var_Z > 0.008856)  var_Z = var_Z ^ ( 1/3 )
else                    var_Z = ( 7.787 * var_Z ) + ( 16 / 116 )
L = ( 116 * var_Y ) - 16
A = 500 * ( var_X - var_Y )
B = 200 * ( var_Y - var_Z )
```

To relatively improve reliability of a color interpretation and/or of a comparison, processing block 90 provides for comparing a set of values of a final digitized color space for a developed shade to a set of values of a final digitized color space for a reference shade. For example, a delta-E value may be determined that is indicative of a minimum distance of a set of L,a,b values of a developed shade from a set of reference L,a,b values of a reference shade. A set of values of a final digitized color space for a developed shade may be compared to a set of values of a final digitized color space for a reference shade as follows:

Compute delta-E. Delta-E is a minimum distance of a measured color shade from multiple shades in a (digital) reference color chart for a chemical parameter.

```
L, A, B (from above)
L(i), A(i), B(i) (These are LAB values of the Reference shades)
xC1 = sqrt( ( A ^ 2 ) + ( B ^ 2 ) )
xC2 = sqrt( ( A(i) ^ 2 ) + ( B(i) ^ 2 ) )
xDL = L(i) - L
xDC = xC2 - xC1
xDE = sqrt( ( ( L - L(i) ) * ( L - L(i) ) )
       +( ( A - A(i) ) * ( A - A(i) ) )
       +( ( B - B(i) ) * ( B - B(i) ) ) )
if ( sqrt( xDE ) > ( sqrt( abs( xDL ) ) + sqrt( abs( xDC ) ) ) ) {
    xDH = sqrt( ( xDE * xDE ) - ( xDL * xDL ) - ( xDC * xDC ) )
}
else {
        xDH = 0
    }
    xSC = 1 + ( 0.045 * xC1 )
    xSH = 1 + ( 0.015 * xC1 )
```

```
    xDL /= 1
    xDC /= 1 * xSC
xDH /= 1 * xSH
Delta E_94 = sqrt( xDL ^ 2 + xDC ^ 2 + xDH ^ 2 )
```

Thus, a color may be automatically compared (e.g, each time a color is read) with a corresponding shade chart to find its closest match (in color space) amongst shades in a pre-stored reference shade chart. For example, each color developed on a test strip may be matched with its corresponding array of shades in a digitized reference shade chart stored in memory (e.g., smart phone memory). In addition, color matching may utilize a CIE XYZ color space rather than an RGB color space to more closely emulate human visual perception. Thereafter, XYZ color space coordinates may be transformed to Lab (Luminosity, a, b) co-ordinates to further improve perceptual uniformity before computing a delta-E color-match value. The smaller the delta-E value between two colors, the better the color match. Thus, rather than only using a relatively simplistic voltage level matching process or an RGB color space for color matching, color matching may be accomplished in a color space that is closer to human visual perception than RGB to match color developed by a test strip to shades of a reference shade chart.

A determination is made at illustrated block 92 whether a match is found. For example, the delta-E color-match value may indicate that a color of a developed shade is within an acceptable range of color for a particular stored reference shade. A range of, e.g., zero to an upper boundary value may be set and checked to determine whether a delta-E color-match value falls within the range of acceptable color for a particular stored reference shade. If a match is found, the quantitative and/or the qualitative value of a chemical parameter for the developed shade is determined by, e.g., identifying the qualitative value and/or the quantitative value associated with the reference shade to which it is matched, and is stored at processing block 98. If a match is not found, processing blocks 94 and 96 may enhance color-matching accuracy by interpolating between adjacent color shades.

In particular, the processing block 94 provides for identifying two smallest delta-E values indicative of two closest reference shades to the developed shade when a match is not found. For example, the processing block 94 identifies the two smallest delta-E values to determine the two closest reference shades in a reference shade chart to the developed shade. In addition, the processing block 94 may identify a qualitative value and/or a quantitative value associated with the two closest reference shades. Conventionally, a color reference (e.g., reference shade chart) that is supplied by a manufacturer may only have a few reference shades (e.g., about 2 to 8 shades, corresponding to 2 to 8 values) for a comparison to a developed color. In this regard, a chemical parameter may be visually measured with a precision of 2 to 8 shades. However, the instant matching process is not limited to a number of color areas, and may interpolate color shades (and/or the corresponding quantitative and quantitative values) as needed using, e.g., the identified two closest reference shades to determine precise values.

The processing block 96 provides for interpolating reference color shades intermediate to the two closest reference shades (e.g., between two adjacent reference shades) and/or interpolating parameter values associated with the interpolated reference color shades. The interpolation may be accomplished at any desired granularity. For example, the granularity may be based on intensity fractions between the two closest reference shades (e.g., intensity fractions of the color green between light green and dark green), based on fractions of a qualitative value between the two closest reference shades (e.g., fractions of "moderate" between a value of "low" and a value of "high"), based on fractions of a quantitative value between the two closest reference shades (e.g., fractions of 0.1 mg/L between a value of 1 mg/L and a value of 2 mg/L), and so on.

An interpolation of color shades between, e.g., two closest reference shades may be completed first before an interpolation of associated parameter values for the interpolated color shades. In this regard, a comparison with a developed shade before interpolation of associated parameter values may identify a matched interpolated color shade and facilitate a calculation for the particular associated parameter value of the particular matched interpolated color shade without unnecessarily wasting resources. In another example, all color shades and all associated parameter values may be interpolated before a comparison with a developed shade. In yet another example, interpolation of color shades between, e.g., two closest reference shades may alternate with a comparison with a developed shade before proceeding to a next interval. Thus, a precise match to a color developed on a test strip (e.g., if it falls between two closest color shades) may be used to facilitate a determination of an intermediate (interpolated) value (e.g., numeric value) for a parameter when a color developed on a test strip is between, e.g., two closest shades on a digitized reference shade chart. The method may iteratively loop back as needed to, e.g., the block processing 82, etc. Processing block 100 provides for displaying quantitative and/or qualitative results to a user. In one example, the results may be forwarded to the application 36 (FIG. 4), discussed above.

It should be understood that a match process may also include any other process discussed herein. Thus, a match process may generally include comparing a set of values for a developed shade with a set of values for a reference shade. In one example, voltage levels corresponding to developed shades of a test strip may be compared with voltage levels corresponding to developed shades of a control test strip determined using known analyte quantities, corresponding to a printed color reference for the same, and so on. In another example, the match process may include comparing a set of values of a digitized color space such as RGB color space for a developed shade with a digitized color space such as RGB color space for a reference shade.

Figure 8:
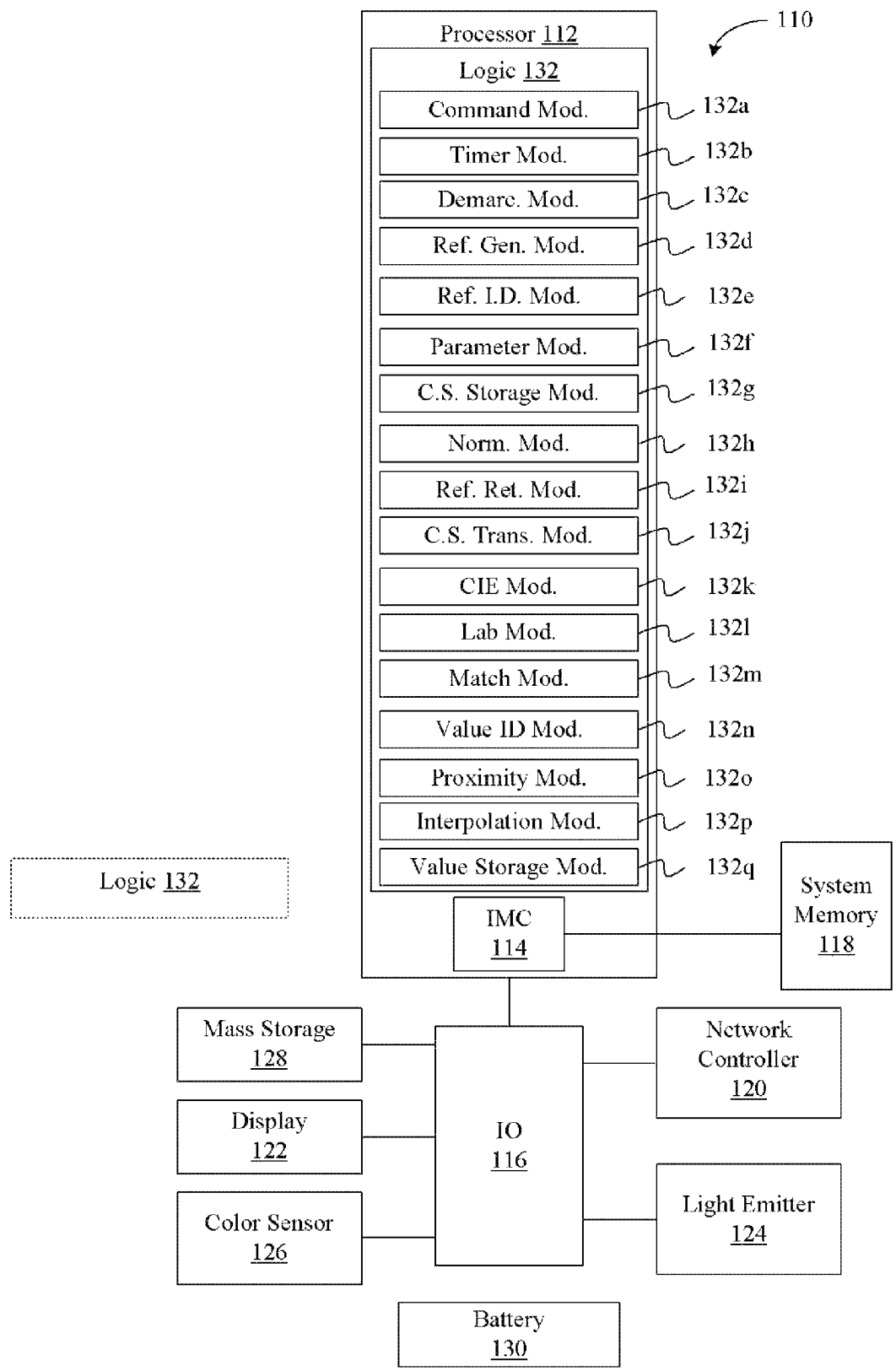
FIG. 8 is a block diagram of an example of a computing system according to an embodiment.

FIG. 8 shows a computing system 110 that may be part of a device having sensor functionality (disaggregated sensor), computing functionality (e.g., PDA, notebook computer, tablet computer, convertible tablet, desktop computer, cloud server), communications functionality (e.g., wireless smart phone, radio), imaging functionality, media playing functionality (e.g., smart television/TV), wearable computer (e.g., headwear, clothing, jewelry, eyewear, etc.) or any combination thereof (e.g., MID). In the illustrated example, the system 110 includes a processor 112, an integrated memory controller (IMC) 114, an input output (IO) module 116, system memory 118, a network controller 120, a display 122, a light emitter 124, one or more sensors 126 (e.g., color sensors, temperature sensors, ambient light sensors, accelerometers), a battery 130 and mass storage 128 (e.g., optical disk, hard disk drive/HDD, flash memory).

The processor 112 may include a core region with one or several processor cores (not shown). The illustrated IO module 116, sometimes referred to as a Southbridge or South Complex of a chipset, functions as a host controller and communicates with the network controller 120, which could provide off-platform communication functionality for a wide variety of purposes such as, for example, cellular telephone (e.g., Wideband Code Division Multiple Access/W-CDMA (Universal Mobile Telecommunications System/UMTS), CDMA2000 (IS-856/IS-2000), etc.), WiFi (Wireless Fidelity, e.g., Institute of Electrical and Electronics Engineers/IEEE 802.11-2007, Wireless Local Area Network/LAN Medium Access Control (MAC) and Physical Layer (PHY) Specifications), 4G LTE (Fourth Generation Long Term Evolution), Bluetooth, WiMax (e.g., IEEE 802.16-2004, LAN/MAN Broadband Wireless LANS), Global Positioning System (GPS), spread spectrum (e.g., 900 MHz), and other radio frequency (RF) telephony purposes. Other standards and/or technologies may also be implemented in the network controller 120.

The network controller 120 may therefore exchange data (e.g., color space values, quantitative values, qualitative values, etc.) with an application 36 (FIG. 4), discussed above. The IO module 116 may also include one or more hardware circuit blocks (e.g., smart amplifiers, analog to digital conversion, integrated sensor hub) to support such wireless and other signal processing functionality.

Although the processor 112 and IO module 116 are illustrated as separate blocks, the processor 112 and IO module 116 may be implemented as a system on chip (SoC) on the same semiconductor die. The system memory 118 may include, for example, double data rate (DDR) synchronous dynamic random access memory (SDRAM, e.g., DDR3 SDRAM JEDEC Standard JESD79-3C, April 2008) modules. The modules of the system memory 118 may be incorporated into a single inline memory module (SIMM), dual inline memory module (DIMM), small outline DIMM (SODIMM), and so forth.

The illustrated processor 112 includes logic 132 (132a-132q, e.g., logic instructions, configurable logic, fixed-functionality hardware logic, etc., or any combination thereof) including a command module 132a to detect a user command, e.g., that modulates a switch, to read a color shade of a color area, a timer module 132b to detect an expiration of a timer to read the color shade of the color area, and a demarcation module 132c to detect a demarcation interval to read the color shade of the color area. The processor 112 includes a reference generation module 132d to generate one of more digitized reference shade charts. The processor 112 includes an identification module 132e to set identification data (e.g., of a printed color reference), a parameter module 132f to set one or more of a number of chemical parameters to be associated with a test strip, a name of each chemical parameter, a number of reference shades for each chemical parameter, and a value (e.g., quantitative, qualitative) of each chemical parameter for each reference shade, and a color space storage module 132g to store a set of values of the initial digitized color space (e.g., in mass storage, system memory, etc.). The processor 112 includes a normalization module 132h to normalize a set of values of the initial digitized color space, and a reference retrieval module 132i to retrieve a digitized color reference from data storage (e.g., memory, system memory, a cloud computing environment, an external mobile computing device, etc.).

The processor 112 includes a color space transformation module 132j to transform one digitized color space to one or more other digitized color spaces. The processor 112 includes an international commission of illumination (CIE) module 132k to convert a Red-Blue-Green color space including a set of Red-Blue-Green values to a CIE XYZ color space including a set of XYZ values, and a Lab module 132l to convert the CIE color space including the set of CIE XYZ values to a Lab color space including a set of L,a,b values. The processor 112 includes a match module 132m to match a final digitized color space of a digitized color reference with a final digitized color space of a digitized test strip (and/or match other values such as voltage values, RGB values, etc.), wherein the match module 132m may determine a delta-E value indicative of a minimum distance of a set of L,a,b values of the developed shade from a set of reference L,a,b values of the reference shade.

The processor 112 includes a value identification module 132n to identify a value (e.g., quantitative, qualitative) of a chemical parameter for the developed shade when a match is found between the developed shade and the reference shade based the determination (e.g., delta-E value). The processor 112 includes a proximity module 132o to make an identification of two smallest delta-E values indicative of two closest reference shades to the developed shade when a match is not found. The processor 112 includes an interpolation module 132p to interpolate a reference shade between the two closest reference shades until a match is found with the developed shade, and to compute the value (e.g., quantitative, qualitative) of the chemical parameter for the developed shade based on the match (e.g., by interpolating the value of the parameter associated with the interpolated reference shade to which the developed shade is matched). The processor 112 includes a value storage module 132q to store a quantitative and/or a qualitative value.

Although the illustrated logic 132 is shown as being implemented on the processor 112, one or more aspects of the logic 132 may be implemented elsewhere such as at a mobile computing platform external to the computing system 110, the color sensor 126, etc., depending on the circumstances. In addition, one or more aspects of the logic 132 may be combined into one or more modules. For example, the reference generation module 132d may include the identification module 132e, the parameter module 132f, and/or the color space storage module 132g. In another example, the color space transformation module 132j may include the CIE module 132k and/or the Lab module 132l. In a further example, the match module 132m may include the value identification module 132n, the proximity module 132o, and/or the interpolation module 132p.

Additional Notes and Examples

Example 1 may include a sensor apparatus to determine a value of a chemical parameter, comprising a housing, one or more light emitters positioned within the housing to emit light through an aperture of the housing, wherein the light to be emitted is to illuminate a color area of a structure that is separable from the housing, and a color sensor positioned within the housing to capture light to be reflected through the aperture and to convert the light to be reflected to an initial digitized color space usable to determine a color shade of the color area, wherein the light to be reflected is to be captured independently at least of a dimension of the color area.

Example 2 may include the sensor apparatus of Example 1, wherein the color sensor is to read the color shade of the color area independently of a spacing between two or more color areas, a number of color areas, a dimension of the structure, and a manufacturer of the structure.

Example 3 may include the sensor apparatus of any one of Example 1 to Example 2, wherein the aperture is positioned at a narrow end of a cone portion of the housing, wherein the color sensor is positioned at a wide end of the cone portion of the housing, and wherein the one or more light emitters are positioned in the cone portion of the housing between the color sensor and the aperture to substantially shield the color sensor from ambient light.

Example 4 may include the sensor apparatus of any one of Example 1 to Example 3, further including a lens is positioned in a cone portion of the housing between the color sensor and the aperture to substantially limit the field of view of the color sensor to that of the aperture.

Example 5 may include the sensor apparatus of any one of Example 1 to Example 4, further including a communication module to forward data to a mobile computing platform external to the housing, wherein the sensor apparatus is a disaggregated sensor.

Example 6 may include the sensor apparatus of any one of Example 1 to Example 5, further including a slit positioned adjacent the aperture and coupled with a cone portion of the housing to accommodate a swipe of the structure through the slit.

Example 7 may include the sensor apparatus of any one of Example 1 to Example 6, further including a command module to detect a user command that modulates a switch to read the color shade of the color area, a timer module to detect an expiration of a timer to read the color shade of the color area, and a demarcation module to detect a demarcation interval to read the color shade of the color area.

Example 8 may include the sensor apparatus of any one of Example 1 to Example 7, wherein the structure includes a printed color reference and each color area includes a reference shade, and wherein the sensor apparatus further includes a reference generation module that includes a reference identification module to set identification data of the printed color reference, a parameter module to set one or more of a number of chemical parameters to be associated with a test strip, a name of each chemical parameter, a number of reference shades for each chemical parameter, and a value of each chemical parameter for each reference shade, and a color space storage module to store a set of values of the initial digitized color space.

Example 9 may include the sensor apparatus of any one of Example 1 to Example 8, wherein the set of values of the initial digitized color space are to be stored in a two-dimensional matrix that includes a color space value set in a first dimension and a chemical parameter-reference shade set in a second dimension.

Example 10 may include the sensor apparatus of any one of Example 1 to Example 9, further including a normalization module to normalize a set of values of the initial digitized color space.

Example 11 may include the sensor apparatus of any one of Example 1 to Example 10, further including a reference retrieval module to retrieve a digitized color reference from data storage.

Example 12 may include the sensor apparatus of any one of Example 1 to Example 11, further including a color space transformation module to convert the initial digitized color space to a final digitized color space, wherein the color space transformation module includes an international commission of illumination (CIE) module to convert a Red-Blue-Green color space including a set of Red-Blue-Green values to a CIE XYZ color space including a set of XYZ values, and a Lab module to convert the CIE color space including the set of CIE XYZ values to a Lab color space including a set of L,a,b values.

Example 13 may include the sensor apparatus of any one of Example 1 to Example 12, wherein the structure includes a test strip and each color area includes a developed shade of the test strip, and wherein the sensor apparatus further includes a match module to match a final digitized color space of a digitized color reference with a final digitized color space of a digitized test strip, wherein the match module is to determine a delta-E value indicative of a minimum distance of a set of L,a,b values of the developed shade from a set of reference L,a,b values of the reference shade, a value identification module to identify a value of a chemical parameter for the developed shade when a match is found between the developed shade and the reference shade based the determination, and a value storage module to store the value.

Example 14 may include the sensor apparatus of any one of Example 1 to Example 13, wherein the match module further includes a proximity module to make an identification of two smallest delta-E values indicative of two closest reference shades to the developed shade when a match is not found, and an interpolation module to interpolate a reference shade between the two closest reference shades until a match is found with the developed shade, and to compute the value of the chemical parameter for the developed shade based on the match.

Example 15 may include a method to determine a value of chemical parameter, comprising providing one or more light emitters positioned within a housing to emit light through an aperture of the housing, wherein the light to be emitted is to illuminate a color area of a structure that is separable from the housing, and providing a color sensor positioned within the housing to capture light to be reflected through the aperture and to convert the light to be reflected to an initial digitized color space usable to determine a color shade of the color area, wherein the light to be reflected is to be captured independently at least of a dimension of the color area.

Example 16 may include the method of Example 15, further including reading the color shade of the color area independently of a spacing between two or more color areas, a number of color areas, a dimension of the structure, and a manufacturer of the structure.

Example 17 may include the method of any one of Example 15 to Example 16, wherein the aperture is positioned at a narrow end of a cone portion of the housing, wherein the color sensor is positioned at a wide end of the cone portion of the housing, and wherein the one or more light emitters are positioned in the cone portion of the housing between the color sensor and the aperture to substantially shield the color sensor from ambient light.

Example 18 may include the method of any one of Example 15 to Example 17, wherein a lens is positioned in a cone portion of the housing between the color sensor and the aperture to substantially limit the field of view of the color sensor to that of the aperture.

Example 19 may include the method of any one of Example 15 to Example 18, further including forwarding data to a mobile computing platform external to the housing, wherein the color sensor is implemented as a disaggregated sensor.

Example 20 may include the method of any one of Example 15 to Example 19, wherein a slit is positioned adjacent the aperture and coupled with a cone portion of the housing to accommodate a swipe of the structure through the slit.

Example 21 may include the method of any one of Example 15 to Example 20, further including detecting a user command that modulates a switch to read the color shade of the color area, detecting an expiration of a timer to read the color shade of the color area, and detecting a demarcation interval to read the color shade of the color area.

Example 22 may include the method of any one of Example 15 to Example 21, wherein the structure includes a printed color reference and each color area includes a reference shade, and wherein the method further includes setting identification data of the printed color reference, setting one or more of a number of chemical parameters to be associated with a test strip, a name of each chemical parameter, a number of reference shades for each chemical parameter, and a value of each chemical parameter for each reference shade, and storing a set of values of the initial digitized color space.

Example 23 may include the method of any one of Example 15 to Example 22, wherein the set of values of the initial digitized color space are to be stored in a two-dimensional matrix that includes a color space value set in a first dimension and a chemical parameter-reference shade set in a second dimension.

Example 24 may include the method of any one of Example 15 to Example 23, further including normalizing a set of values of the initial digitized color space.

Example 25 may include the method of any one of Example 15 to Example 24, further including retrieve a digitized color reference from data storage.

Example 26 may include the method of any one of Example 15 to Example 25, further including converting the initial digitized color space to a final digitized color space, wherein the method further includes converting a Red-Blue-Green color space including a set of Red-Blue-Green values to an international commission of illumination (CIE) XYZ color space including a set of XYZ values, and converting the CIE color space including the set of CIE XYZ values to a Lab color space including a set of L,a,b values.

Example 27 may include the method of any one of Example 15 to Example 26, wherein the structure includes a test strip and each color area includes a developed shade of the test strip, and wherein the method further includes matching a final digitized color space of a digitized color reference with a final digitized color space of a digitized test strip, wherein the match module is to determine a delta-E value indicative of a minimum distance of a set of L,a,b values of the developed shade from a set of reference L,a,b values of the reference shade, identifying a value of a chemical parameter for the developed shade when a match is found between the developed shade and the reference shade based the determination, and storing the value.

Example 28 may include the method of any one of Example 15 to Example 27, further including identifying two smallest delta-E values indicative of two closest reference shades to the developed shade when a match is not found, interpolating a reference shade between the two closest reference shades until a match is found with the developed shade, and computing the value of the chemical parameter for the developed shade based on the match.

Example 29 may include at least one computer readable storage medium comprising one or more instructions that when executed on a computing device cause the computing device to emit light through an aperture of a housing, wherein the light to be emitted is to illuminate a color area of a structure that is separable from the housing, and capture light to be reflected through the aperture and convert the light to be reflected to an initial digitized color space usable to determine a color shade of the color area, wherein the light to be reflected is to be captured independently at least of a dimension of the color area.

Example 30 may include the at least one computer readable storage medium of Example 29, wherein when executed the one or more instructions cause the computing device to read the color shade of the color area independently of a spacing between two or more color areas, a number of color areas, a dimension of the structure, and a manufacturer of the structure.

Example 31 may include the at least one computer readable storage medium of any one of Example 29 to Example 30, wherein the aperture is positioned at a narrow end of a cone portion of the housing, wherein a color sensor is positioned at a wide end of the cone portion of the housing, and wherein one or more light emitters are positioned in the cone portion of the housing between the color sensor and the aperture to substantially shield the color sensor from ambient light.

Example 32 may include the at least one computer readable storage medium of any one of Example 29 to Example 31, wherein a lens is positioned in a cone portion of the housing between a color sensor and the aperture to substantially limit the field of view of the color sensor to that of the aperture.

Example 33 may include the at least one computer readable storage medium of any one of Example 29 to Example 32, wherein when executed the one or more instructions cause the computing device to forward data to a mobile computing platform external to the housing, wherein a color sensor is to be implemented as a disaggregated sensor.

Example 34 may include the at least one computer readable storage medium of any one of Example 29 to Example 33, wherein a slit is positioned adjacent the aperture and coupled with a cone portion of the housing to accommodate a swipe of the structure through the slit.

Example 35 may include the at least one computer readable storage medium of any one of Example 29 to Example 34, wherein when executed the one or more instructions cause the computing device to detect a user command that modulates a switch to read the color shade of the color area, detect an expiration of a timer to read the color shade of the color area, and detect a demarcation interval to read the color shade of the color area.

Example 36 may include the at least one computer readable storage medium of any one of Example 29 to Example 35, wherein the structure includes a printed color reference and each color area includes a reference shade, and wherein when executed the one or more instructions cause the computing device to set identification data of the printed color reference, set one or more of a number of chemical parameters to be associated with a test strip, a name of each chemical parameter, a number of reference shades for each chemical parameter, and a value of each chemical parameter for each reference shade, and store a set of values of the initial digitized color space.

Example 37 may include the at least one computer readable storage medium of any one of Example 29 to Example 36, wherein the set of values of the initial digitized color space are to be stored in a two-dimensional matrix that includes a color space value set in a first dimension and a chemical parameter-reference shade set in a second dimension.

Example 38 may include the at least one computer readable storage medium of any one of Example 29 to Example 37, wherein when executed the one or more instructions cause the computing device to normalize a set of values of the initial digitized color space.

Example 39 may include the at least one computer readable storage medium of any one of Example 29 to Example 38, wherein when executed the one or more instructions cause the computing device to retrieve a digitized color reference from data storage.

Example 40 may include the at least one computer readable storage medium of any one of Example 29 to Example 39, wherein when executed the one or more instructions cause the computing device to convert the initial digitized color space to a final digitized color space by a conversion of a Red-Blue-Green color space including a set of Red-Blue-Green values to an international commission of illumination (CIE) XYZ color space including a set of XYZ values, and a conversion of the CIE color space including the set of CIE XYZ values to a Lab color space including a set of L,a,b values.

Example 41 may include the at least one computer readable storage medium of any one of Example 29 to Example 40, wherein the structure includes a test strip and each color area includes a developed shade of the test strip, and wherein when executed the one or more instructions cause the computing device to match a final digitized color space of a digitized color reference with a final digitized color space of a digitized test strip, wherein the match is to determine a delta-E value indicative of a minimum distance of a set of L,a,b values of the developed shade from a set of reference L,a,b values of the reference shade, identify a value of a chemical parameter for the developed shade when a match is found between the developed shade and the reference shade based the determination, and store the value.

Example 42 may include the at least one computer readable storage medium of any one of Example 29 to Example 41, wherein when executed the one or more instructions cause the computing device to identify two smallest delta-E values indicative of two closest reference shades to the developed shade when a match is not found, interpolate a reference shade between the two closest reference shades until a match is found with the developed shade, and compute the value of the chemical parameter for the developed shade based on the match.

Example 43 may include a sensor apparatus system to determine a value of chemical parameter, comprising means for performing the method of any one of Example 15 to Example 28.

Example 44 may include a sensor apparatus to determine a value of a chemical parameter, comprising a housing, one or more light emitters positioned within the housing and facing a structure that is separable from the housing to illuminate a color area of the structure with light to be emitted through an aperture of the housing, and a color sensor positioned within the housing and facing the aperture to read a color shade of the color area independently at least of a dimension of the color area, wherein light to be reflected back from the color area through the aperture is to be captured by the color sensor and converted to an initial digitized color space to be used to determine the color shade of the color area.

Example 45 may include the sensor apparatus of example 44, and further include the sensor apparatus of any one of Example 1 to Example 14.

Example 46 may include a method to determine a value of chemical parameter, comprising illuminating a color area of the structure that is separable from a housing through an aperture of the housing via one or more light emitters positioned within the housing and facing the structure, and reading a color shade of the color area independently at least of a dimension of the color area via a color sensor positioned within the housing and facing the aperture, wherein light reflected back from the color area through the aperture is captured by the color sensor and converted to an initial digitized color space to be used to determine the color shade of the color area.

Example 47 may include the method of example 46, and further include the method of any one of Example 15 to Example 28.

Example 48 may include at least one computer readable storage medium comprising one or more instructions that when executed on a computing device cause the computing device to illuminate a color area of the structure that is separable from a housing through an aperture of the housing via one or more light emitters positioned within the housing and facing the structure, and read a color shade of the color area independently at least of a dimension of the color area via a color sensor positioned within the housing and facing the aperture, wherein light to be reflected back from the color area through the aperture is to be captured by the color sensor and converted to an initial digitized color space to be used to determine the color shade of the color area.

Example 49 may include the at least one computer readable storage medium of example 48, and further include the at least one computer readable storage medium of any one of Example 29 to Example 42.

Example 50 may include a sensor apparatus system to determine a value of chemical parameter, comprising means for performing the method of any one of Example 44 to Example 45.

Thus, a sensor apparatus and techniques may be implemented for substantially all type of off-the-shelf paper test strips from substantially any manufacturer. The apparatus and techniques work with substantially any size/shape/dimension of the test strip, any number of color areas and any type of ordering or spacing between color areas of the test strip, and/or any kind of color shades and any number of color shades per color area, irrespective of which chemical parameters correspond to the color areas. In addition, it may be possible to convert substantially any type of paper-based reference shade chart to digital representation, thereby enabling automatic color matching. Moreover, a disaggregated color sensor may be utilized that is not substantially affected by ambient light, and/or that may provide its own controlled light source to illuminate and sense color areas, e.g., on test strips. The disaggregation allows a color sensor to be moved and placed on each color area to read any type of off-the-shelf test strips, irrespective of size, shape of the strip, and irrespective of the number of color areas or spacing between the color areas, and so on. Thus, a sensor apparatus may not require a pre-designed slit size for insertion of test strip and/or a pre-designed number of optical sensors at a pre-defined spacing tightly integrated inside a customized reader device, and therefore may not be limited to reading only compatible test strips from a particular manufacturer.

Embodiments are applicable for use with all types of semiconductor integrated circuit ("IC") chips. Examples of these IC chips include but are not limited to processors, controllers, chipset components, programmable logic arrays (PLAs), memory chips, network chips, systems on chip (SoCs), SSD/NAND controller ASICs, and the like. In addition, in some of the drawings, signal conductor lines are represented with lines. Some may be different, to indicate more constituent signal paths, have a number label, to indicate a number of constituent signal paths, and/or have arrows at one or more ends, to indicate primary information flow direction. This, however, should not be construed in a limiting manner. Rather, such added detail may be used in connection with one or more exemplary embodiments to facilitate easier understanding of a circuit. Any represented signal lines, whether or not having additional information, may actually comprise one or more signals that may travel in multiple directions and may be implemented with any suitable type of signal scheme, e.g., digital or analog lines implemented with differential pairs, optical fiber lines, and/or single-ended lines.

Example sizes/models/values/ranges may have been given, although embodiments are not limited to the same. As manufacturing techniques (e.g., photolithography) mature over time, it is expected that devices of smaller size could be manufactured. In addition, well known power/ground connections to IC chips and other components may or may not be shown within the figures, for simplicity of illustration and discussion, and so as not to obscure certain aspects of the embodiments. Further, arrangements may be shown in block diagram form in order to avoid obscuring embodiments, and also in view of the fact that specifics with respect to implementation of such block diagram arrangements are highly dependent upon the platform within which the embodiment is to be implemented, i.e., such specifics should be well within purview of one skilled in the art. Where specific details (e.g., circuits) are set forth in order to describe example embodiments, it should be apparent to one skilled in the art that embodiments can be practiced without, or with variation of, these specific details. The description is thus to be regarded as illustrative instead of limiting.

The term "coupled" may be used herein to refer to any type of relationship, direct or indirect, between the components in question, and may apply to electrical, mechanical, fluid, optical, electromagnetic, electromechanical or other connections. In addition, the terms "first", "second", etc. may be used herein only to facilitate discussion, and carry no particular temporal or chronological significance unless otherwise indicated.

As used in this application and in the claims, a list of items joined by the term "one or more of" or "at least one of" may mean any combination of the listed terms. For example, the phrases "one or more of A, B or C" may mean A, B, C; A and B; A and C; B and C; or A, B and C.

Those skilled in the art will appreciate from the foregoing description that the broad techniques of the embodiments can be implemented in a variety of forms. Therefore, while the embodiments have been described in connection with particular examples thereof, the true scope of the embodiments should not be so limited since other modifications will become apparent to the skilled practitioner upon a study of the drawings, specification, and following claims.

We claim:

1. A sensor apparatus comprising:
a housing;
one or more light emitters positioned within the housing and coupled with an aperture of the housing to emit light through the aperture of the housing, wherein the light to be emitted from the one or more light emitters is to illuminate a color area of a structure that is separable from the housing, and wherein the structure includes a test strip and the color area includes a developed shade;
a color sensor positioned within the housing and coupled with the aperture of the housing to capture light to be reflected through the aperture from the color area and to convert the light to be reflected to an initial digitized color space usable to determine the developed shade of the color area, wherein the light to be reflected is to be captured independently at least of a dimension of the color area;
a match module to match a final digitized color space of a digitized color reference including a reference shade with a final digitized color space of the test strip, wherein the match module is to make a determination of a delta-E value indicative of a minimum distance of a set of L,a,b values of the developed shade from a set of reference L,a,b values of the reference shade;
a value identification module to identify a value of a chemical parameter for the developed shade when a match is found between the developed shade and the reference shade based the determination; and
a value storage module to store the value.

2. The sensor apparatus of claim 1, wherein the color sensor is to read the developed shade of the color area independently of a spacing between two or more color areas, a number of color areas, a dimension of the structure, and a manufacturer of the structure.

3. The sensor apparatus of claim 1, wherein the aperture is positioned at a narrow end of a cone portion of the housing, wherein the color sensor is positioned at a wide end of the cone portion of the housing, and wherein the one or more light emitters are positioned in the cone portion of the housing between the color sensor and the aperture to substantially shield the color sensor from ambient light.

4. The sensor apparatus of claim 1, further including a lens positioned in a cone portion of the housing between the color sensor and the aperture to substantially limit a field of view of the color sensor to that of the aperture.

5. The sensor apparatus of claim 1, further including a communication module to forward data to a mobile computing platform external to the housing, wherein the sensor apparatus is a disaggregated sensor.

6. The sensor apparatus of claim 1, further including a slit positioned adjacent the aperture and coupled with a cone portion of the housing to accommodate a swipe of the structure through the slit.

7. The sensor apparatus of claim 1, further including:
a command module to detect a user command that modulates a switch to read the developed shade of the color area;
a timer module to detect an expiration of a timer to read the developed shade of the color area; and
a demarcation module to detect a demarcation interval to read the developed shade of the color area.

8. The sensor apparatus of claim 1, further includes further including a reference generation module that includes:
a reference identification module to set identification data of a printed color reference;
a parameter module to set one or more of a number of chemical parameters to be associated with the test strip, a name of each of the chemical parameters, a number of reference shades for each of the chemical parameters, and a value of each of the chemical parameters for each of the reference shades; and
a color space storage module to store a set of values of an initial digitized color space of the digitized color reference.

9. The sensor apparatus of claim 8, wherein a set of values of the initial digitized color space of the digitized color reference are to be stored in a two-dimensional matrix that includes a color space value set in a first dimension and a chemical parameter-reference shade set in a second dimension.

10. The sensor apparatus of claim 1, further including a normalization module to normalize a set of values of the initial digitized color space.

11. The sensor apparatus of claim 1, further including a reference retrieval module to retrieve the digitized color reference from data storage.

12. The sensor apparatus of claim 1, further including a color space transformation module to convert the initial digitized color space to the final digitized color space, wherein the color space transformation module includes:
an international commission of illumination (CIE) module to convert a Red-Blue-Green color space including a set of Red-Blue-Green values to a CIE XYZ color space including a set of XYZ values; and
a Lab module to convert the CIE color space including the set of CIE XYZ values to a Lab color space including the set of L,a,b values.

13. The sensor apparatus of 1, wherein the match module further includes:
a proximity module to make an identification of two smallest delta-E values indicative of two closest reference shades to the developed shade when a match is not found; and
an interpolation module to interpolate a reference shade between the two closest reference shades until a match is found with the developed shade, and to compute the value of the chemical parameter for the developed shade based on the match.

14. A method comprising:
providing one or more light emitters positioned within a housing and coupled with an aperture of the housing to emit light through the aperture of the housing, wherein the light to be emitted from the one or more light emitters is to illuminate a color area of a structure that is separable from the housing, and wherein the structure includes a test strip and the color area includes a developed shade;
providing a color sensor positioned within the housing and coupled with the aperture of the housing to capture light to be reflected through the aperture from the color area and to convert the light to be reflected to an initial digitized color space usable to determine a developed shade of the color area, wherein the light to be reflected is to be captured independently at least of a dimension of the color area
matching a final digitized color space of a digitized color reference including a reference shade with a final digitized color space of the test strip, wherein a determination is made of a delta-E value indicative of a minimum distance of a set of L,a,b values of the developed shade from a set of reference L,a,b values of the reference shade;
identifying a value of a chemical parameter for the developed shade when a match is found between the developed shade and the reference shade based the determination; and
storing the value.

15. The method of claim 14, wherein the aperture is positioned at a narrow end of a cone portion of the housing, wherein the color sensor is positioned at a wide end of the cone portion of the housing, and wherein the one or more light emitters are positioned in the cone portion of the housing between the color sensor and the aperture to substantially shield the color sensor from ambient light.

16. The method of claim 14, further including:
setting identification data of a printed color reference;
setting one or more of a number of chemical parameters to be associated with the test strip, a name of each of the chemical parameters, a number of reference shades for each of the chemical parameters, and a value of each of the chemical parameters for each of the reference shades; and
storing a set of values of an initial digitized color space of the digitized color reference.

17. The method of claim 14, further including converting the initial digitized color space to the final digitized color space, wherein the method further includes:
converting a Red-Blue-Green color space including a set of Red-Blue-Green values to an international commission of illumination (CIE) XYZ color space including a set of XYZ values; and
converting the CIE color space including the set of CIE XYZ values to a Lab color space including the set of L,a,b values.

18. The method of 14, further including:
identifying two smallest delta-E values indicative of two closest reference shades to the developed shade when a match is not found;
interpolating a reference shade between the two closest reference shades until a match is found with the developed shade; and
computing the value of the chemical parameter for the developed shade based on the match.

19. At least one computer readable storage medium comprising one or more instructions that when executed on a computing device cause the computing device to:
emit light through an aperture of a housing from one or more light emitters positioned within the housing and coupled with the aperture of the housing, wherein the light to be emitted from the one or more light emitters is to illuminate a color area of a structure that is separable from the housing, and wherein the structure includes a test strip and the color area includes a developed shade;
capture light at a color sensor positioned within the housing and coupled with the aperture of the housing that is to be reflected through the aperture from the color area and convert the light to be reflected to an initial digitized color space usable to determine the developed shade of the color area, wherein the light to be reflected is to be captured independently at least of a dimension of the color area;
match a final digitized color space of a digitized color reference including a reference shade with a final digitized color space of the test strip, wherein a determination is to be made of a delta-E value indicative of a minimum distance of a set of L,a,b values of the developed shade from a set of reference L,a,b values of the reference shade;
identify a value of a chemical parameter for the developed shade when a match is found between the developed shade and the reference shade based the determination; and
store the value.

20. The at least one medium of claim 19, wherein when executed the one or more instructions cause the computing device to:
set identification data of a printed color reference;
set one or more of a number of chemical parameters to be associated with the test strip, a name of each of the chemical parameters, a number of reference shades for each of the chemical parameters, and a value of each of the chemical parameters for each of the reference shades; and store a set of values of an initial digitized color space of the digitized color reference.

21. The at least one medium of claim 19, wherein when executed the one or more instructions cause the computing device to convert the initial digitized color space to the final digitized color space by:

a conversion of a Red-Blue-Green color space including a set of Red-Blue-Green values to an international commission of illumination (CIE) XYZ color space including a set of XYZ values; and a conversion of the CIE color space including the set of CIE XYZ values to a Lab color space including the set of L,a,b values.

22. The at least one medium of claim 19, wherein when executed the one or more instructions cause the computing device to:

identify two smallest delta-E values indicative of two closest reference shades to the developed shade when a match is not found;

interpolate a reference shade between the two closest reference shades until a match is found with the developed shade; and compute the value of the chemical parameter for the developed shade based on the match.

23. A sensor apparatus comprising:

a housing;

one or more light emitters positioned within the housing and coupled with an aperture of the housing to emit light through the aperture of the housing, wherein the light to be emitted from the one or more light emitters is to illuminate a color area of a structure that is separable from the housing;

a color sensor positioned within the housing and coupled with the aperture of the housing to capture light to be reflected through the aperture from the color area and to convert the light to be reflected to an initial digitized color space usable to determine a color shade of the color area, wherein the light to be reflected is to be captured independently at least of a dimension of the color area; and a slit positioned adjacent the aperture and coupled with a cone portion of the housing to accommodate a swipe of the structure through the slit.

24. A sensor apparatus comprising:

a housing;

one or more light emitters positioned within the housing and coupled with an aperture of the housing to emit light through the aperture of the housing, wherein the light to be emitted from the one or more light emitters is to illuminate a color area of a structure that is separable from the housing;

a color sensor positioned within the housing and coupled with the aperture of the housing to capture light to be reflected through the aperture from the color area and to convert the light to be reflected to an initial digitized color space usable to determine a color shade of the color area, wherein the light to be reflected is to be captured independently at least of a dimension of the color area;

a command module to detect a user command that modulates a switch to read the color shade of the color area;

a timer module to detect an expiration of a timer to read the color shade of the color area; and a demarcation module to detect a demarcation interval to read the color shade of the color area.

25. A sensor apparatus comprising:

a housing;

one or more light emitters positioned within the housing and coupled with an aperture of the housing to emit light through the aperture of the housing, wherein the light to be emitted from the one or more light emitters is to illuminate a color area of a structure that is separable from the housing, and wherein the structure includes a printed color reference and the color area includes a reference shade;

a color sensor positioned within the housing and coupled with the aperture of the housing to capture light to be reflected through the aperture from the color area and to convert the light to be reflected to an initial digitized color space usable to determine the reference shade of the color area, wherein the light to be reflected is to be captured independently at least of a dimension of the color area; and a reference generation module that includes:

a reference identification module to set identification data of a printed color reference;

a parameter module to set one or more of a number of chemical parameters to be associated with a test strip, a name of each of the chemical parameters, a number of reference shades for each of the chemical parameters, and a value of each of the chemical parameters for each of the reference shades; and a color space storage module to store a set of values of the initial digitized color space.

26. A sensor apparatus comprising:

a housing;

one or more light emitters positioned within the housing and coupled with an aperture of the housing to emit light through the aperture of the housing, wherein the light to be emitted from the one or more light emitters is to illuminate a color area of a structure that is separable from the housing;

a color sensor positioned within the housing and coupled with the aperture of the housing to capture light to be reflected through the aperture from the color area and to convert the light to be reflected to an initial digitized color space usable to determine a color shade of the color area, wherein the light to be reflected is to be captured independently at least of a dimension of the color area; and a normalization module to normalize a set of values of the initial digitized color space.

27. A sensor apparatus comprising:

a housing;

one or more light emitters positioned within the housing and coupled with an aperture of the housing to emit light through the aperture of the housing, wherein the light to be emitted from the one or more light emitters is to illuminate a color area of a structure that is separable from the housing;

a color sensor positioned within the housing and coupled with the aperture of the housing to capture light to be reflected through the aperture from the color area and to convert the light to be reflected to an initial digitized color space usable to determine a color shade of the color area, wherein the light to be reflected is to be captured independently at least of a dimension of the color area; and a color space transformation module to convert the initial digitized color space to a final digitized color space, wherein the color space transformation module includes:
an international commission of illumination (CIE) module to convert a Red-Blue-Green color space including a set of Red-Blue-Green values to a CIE XYZ color space including a set of XYZ values; and
a Lab module to convert the CIE color space including the set of CIE XYZ values to a Lab color space including a set of L,a,b values.

* * * * *

UNITED STATES PATENT AND TRADEMARK OFFICE
CERTIFICATE OF CORRECTION

PATENT NO. : 9,568,432 B2  
APPLICATION NO. : 14/497384  
DATED : February 14, 2017  
INVENTOR(S) : Baxi et al.

Page 1 of 1

It is certified that error appears in the above-identified patent and that said Letters Patent is hereby corrected as shown below:

In the Claims

At Column 24, Claim number 8, Line number 48, after "claim 1", delete "further includes"

At Column 25, Claim number 14, Line number 47, delete "area", and insert --area;--

At Column 26, Claim number 18, Line number 21, after "of", insert --claim--

Signed and Sealed this  
Nineteenth Day of June, 2018

Andrei Iancu  
*Director of the United States Patent and Trademark Office*